United States Patent
Ordonez Jacome

(10) Patent No.: US 7,261,910 B2
(45) Date of Patent: Aug. 28, 2007

(54) METHOD OF OBTAINING AND TREATING COMPOUNDS FROM OZONIZED UNSATURATED VEGETABLE OILS FOR PHARMACEUTICAL COMPOSITIONS FOR MEDICAL AND VETERINARY USE

(76) Inventor: Neptali Rene Cristobal Ordonez Jacome, M. Tamayo E13-35 Y de las Uvas, Quito (EC)

( * ) Notice: Subject to any disclaimer, the term of this patent is extended or adjusted under 35 U.S.C. 154(b) by 0 days.

(21) Appl. No.: 10/545,497

(22) PCT Filed: Nov. 6, 2003

(86) PCT No.: PCT/EC03/00005

§ 371 (c)(1), (2), (4) Date: Aug. 12, 2005

(87) PCT Pub. No.: WO2004/071477

PCT Pub. Date: Aug. 26, 2004

(65) Prior Publication Data

US 2006/0153939 A1 Jul. 13, 2006

(30) Foreign Application Priority Data

Feb. 14, 2003 (EC) ..................... 03-4481

(51) Int. Cl.
*A61K 36/185* (2006.01)
(52) U.S. Cl. .................................... 424/776
(58) Field of Classification Search ............... None
See application file for complete search history.

(56) References Cited

U.S. PATENT DOCUMENTS

| | | | |
|---|---|---|---|
| 4,591,602 A | * | 5/1986 | De Villez ............... 514/463 |
| 4,983,637 A | | 1/1991 | Herman |
| 5,183,911 A | * | 2/1993 | Washuttl et al. ............ 554/181 |
| 5,190,979 A | * | 3/1993 | Herman ....................... 514/762 |

FOREIGN PATENT DOCUMENTS

| | | | |
|---|---|---|---|
| ES | 2192586 | * | 12/2001 |
| ES | 2162586 B1 | | 7/2002 |
| JP | 58-177908 | * | 10/1983 |
| JP | 58177908 A | | 10/1983 |
| JP | 2000-351985 A | * | 12/2000 |
| WO | WO96/25409 | * | 8/1996 |

OTHER PUBLICATIONS

1999. Hamme et al. Antimicrobial activity of essential oils and other plant extracts. Journal of Applied Microbiology. 89. pp. 985-990.*

* cited by examiner

*Primary Examiner*—Christopher R. Tate
*Assistant Examiner*—Melenie McCormick
(74) *Attorney, Agent, or Firm*—James C. Eaves, Jr.; Greenebaum Doll & McDonald PLLC

(57) ABSTRACT

The invention relates to a method of obtaining a stable product of natural vegetable origin, particularly macadamia oil, which is treated in a reactor in which the oil is exposed to a continuous flow of ozone and, subsequently to a feedback of end gases under the influence of an electromagnetic field. The treatment and production time is significantly reduced under specific conditions in terms of temperature, pressure, gas streams, pH and substance saturation volumes with ozone, which is obtained in an oxygen-fed generator. According to the invention, the reaction causes the formation of a novel compound: topically-applied ozone cream which is used to treat infectious processes. The inventive ozonized cream can penetrate and regenerate the epithelial tissue without causing skin irritations associated with similar known treatment methods. The compound is stable and the fundamental nature thereof does not tend to alter.

25 Claims, No Drawings

METHOD OF OBTAINING AND TREATING COMPOUNDS FROM OZONIZED UNSATURATED VEGETABLE OILS FOR PHARMACEUTICAL COMPOSITIONS FOR MEDICAL AND VETERINARY USE

In U.S. Pat. No. 5,190,979, Herman writes about adding products like propylene glycol, propyl paraben and glycerine to ozonized linalool cream for treating acne and adding glycerine and polyentilene glycol, among other compounds, for treating burns. He does not mention whether these produce secondary effects.

No synthetic product is added to this invention that uses macadamia oil and the results of tests on human beings showed no secondary effects. Prior researchers performed their work using rabbit skin.

DISCLOSURE OF THE INVENTION

The invention specifically involves the ozonation of macadamia oil and the derivative fatty acids, monoterpene oxides, and aldehydes.

The ozone may be added to the double bonds present in the structure of the oils through the Criegee process that generates the formation of ozonides. These ozonides are unstable in hydrophilic environments and break down, causing the rupture of the chain at that point. But in hydrophobic environments, these ozonides are stable, leading to an increase in the substance's molecular weight since three atoms of oxygen are incorporated into the molecular structure for each double bond. This can lead to the substance's change of state.

This reaction process is slow, and energy is required to accelerate it. This energy can be added through heat or other specific forms, such as an electromagnetic field, that effects the movement of each molecule that rotates because of the energy. The rotation of molecules, positioned by the field that is applied, results in an increase in the internal temperature of the system and a higher frequency of collisions between molecules. The energy that is applied through electromagnetic fields is suitable for the ozone-gas diffusion process in the oil-liquid medium and the formation reaction of ozonides.

The fatty acids, which are essential components of the human body, enter in the form of triacylglycerol, are a source of energy, and play an important role in the membrane structure. In 1929, Burr discovered that some are resynthesized by animals, while others are produced by plants. It is known that palmito, stearic, palmitoleic, and oleic have a dual origin; linoleic and alpha linoleic are produced by plants. The reactions are produced by stages of desaturation and elongation. 66-dalton enzymes (Okayasu et. al. 1981) specifically produce a double bridge between carbons 6 and 7 and are strategically located at the beginning of the biosynthetic scheme.

When the enzymes are located in the endoplasmic reticular membrane (Brener 1974), an action has recently (sic) been observed in the mitochondrial fraction.

The invention involves the pure macadamia oil being exposed to ozone in a reactor using an electromagnetic field in a frequency range between 140 and 650 MHz (the work done by Rasplicka, from Yanko industries, used very low frequencies—50-60 Hz).

A 2-kg load of macadamia oil is used with a 5 and 25 lt/min flow of ozone, at a concentration that varies between 4 and 26 g/h. The temperature range between the initial and final phases is between 2 and 35 degrees Celsius, and the working and process time is between 8 and 25 hours. Other inventors achieved a process time of between 180 and 300 hours (Washuttl et. al., U.S. Pat. No. 5,183,911).

The micro-bubbling through the reactor column should be continuous, especially in order to achieve the solid consistency that results when working at a lower atmospheric pressure, one that corresponds to an altitude of 2800 meters above sea level (distinguishing this process from those of other investigators who work at sea level, Ozone Research Center, National Center of Scientific Research—Cuba) and with environmental temperatures that fluctuate between 5 and 20 degrees Celsius. Another accomplishment is a mechanism of reverse-feeding in the upper part of the column so that the elements that are attracted are reincorporated in the process. All of these procedures yield surprising and unexpected positive results. These new procedures were not developed by similar processes, which sets them apart from the methods of other researchers who do not reinject the gases and do not use electromagnetic fields. (Herman et. al U.S. Pat. Nos. 4,983,637 and 5,190,979).

The compound obtained using this procedure is a cream with an ozone saturation of between 60% and 95% that can be used directly on the skin; and it has been shown [that the cream] does not cause secondary effects.

EXAMPLES

The following examples are provided to illustrate the invention and should not be considered as limits on its reach.

Example 1

Obtaining ozonized cream from macadamia oil.

A 2-kg load of pure macadamia oil is placed in the reactor. The ozone is diffused through the reactor under the influence of the electromagnetic field. The flow of gas is from 5 to 25 liters per minute and the ozone concentration varies from 4 to 26 g/h. The ozonization takes place for several hours, until the mix has a doughy consistency. The whole time, the exhaust gases are fed back into the process. Then the temperature is changed and the final product is extracted without using any additional chemical. After noting the pH, the product is ready to be bottled and labeled.

Efficacy Trial 1. Third-Degree Burns.

The cream was applied to 8 patients with extensive second- and third-degree burns on the skin and with skin grafts showing signs of rejection.

The treatments were applied after removing the dead tissue. A generous layer of the product was applied to the extensive effected areas of skin, which was then covered with sterile gauze. These treatments, which were repeated daily for 6 weeks, achieved the following results:

The skin completely regenerated

No additional infections were observed

The gauze was less likely to stick to the wound

The skin grafts were not rejected

There was a reduction in the formation of scabs, which are hard and painful. Furthermore, when the burns are treated with conventional pharmaceuticals, the scabs leave marks when they fall away.

There were no keloids (excessive growth of soft and elevated tissue that can occur in third-degree burns)

The patient with the largest burn area, having burns covering 18% of his body, took 6 weeks. Patients with less extensive burns recovered more quickly. The study was performed double blind.

Efficacy Trial 2. Bed Sores.

Six patients were chosen who had developed bed sores from multiple traumas or quadriplegia after suffering a traffic accident.

The ulcers showed a loss of [tissue matter] in an average area of 4 to 15 cm². The patients were between 22 and 70 years old and showed no signs of metabolic diseases, so the cream was applied twice a day for 10 days.

Antibiotics were not used and the general management of the patients was made based on the condition of the main pathology.

After 10 days, the following results were observed:

The ulcers closed completely.

No scabs formed.

The color of the skin was uniform compared with the skin in the surrounding area, except in colored patients.

The new skin tissue showed no signs of being fragile as occurs on the surface of skin that has been under pressure and has received reduced blood flow.

In the three patients who had smaller wounds, the wounds closed in less than 10 days. The study was double blind and evaluated skin-rehabilitation creams with synthetic active ingredients.

The invention claimed is:

1. A method for obtaining an ozonized macadamia oil composition, comprising the steps of:
   a. placing a quantity of pure macadamia oil in a vertical reactor; and,
   b. diffusing ozone for a period of between 8 and 25 hours in a concentration of between 4 and 26 grams per hour through the reactor under the influence of an electromagnetic field.

2. The method of claim 1, wherein exhaust gases are formed and wherein the exhaust gases are injected back into the reactor.

3. The method of claim 1 where the electromagnetic field has a frequency of between 140 and 650 MHz.

4. The method of claim 1 where the ozone has a flow rate of between 5 and 25 liters per minute.

5. The method of claim 1 where the step of diffusing ozone has an initial phase temperature and a final phase temperature and where said final phase temperature is greater than said initial phase temperature.

6. The method of claim 1 whereby the step of diffusing ozone causes the ozonized macadamia oil composition to have a doughy consistency.

7. An ozonized macadamia oil composition where ozone comprises between 50% and 95% of the total composition, whereby the composition is made by the method of claim 1.

8. The ozonized macadamia oil composition of claim 7, further comprising one of gadoleic or arachidic acid, C16 to C20 in a concentration between 0.05% and 8% of total weight.

9. The ozonized macadamia oil composition of claim 7, further comprising one of terpene aldehyde or monoterpene oxide in a concentration between 0.05% and 4% of total weight.

10. The ozonized macadamia oil composition of claim 7, further comprising one of 1,8 cineol, 16 methyl heptadecanoic acid, or 14 methyl hexadecanoic acid in a concentration between 0.05% and 3% of total weight.

11. The ozonized macadamia oil composition of claim 7 where said composition is a cream having a crystalline quality.

12. The ozonized macadamia oil composition of claim 7 where said composition can be applied topically to skin which has had its anatomical structure affected.

13. The ozonized macadamia oil composition of claim 7 where said composition is impregnated into a sterile cotton gauze to a point of saturation.

14. A method for obtaining an ozonized macadamia oil composition, comprising the steps of:
   a. placing a quantity of pure macadamia oil in a vertical reactor; and,
   b. diffusing ozone in a concentration of between 4 and 26 grams per hour through the reactor under the influence of an electromagnetic filed, whereby this step of diffusing ozone causes the ozonized macadamia oil composition to have a doughy consistency.

15. The step of method 14, wherein exhaust gases are formed and wherein the exhaust gases are injected back into the reactor.

16. The method of claim 14 where the electromagnetic field has a frequency of between 140 and 650 MHz.

17. The method of claim 14 where the ozone has a flow rate of between 5 and 25 liters per minute.

18. The method of claim 14 where the step of diffusing ozone has an initial phase temperature and a final phase temperature and where said final phase temperature is greater than said initial phase temperature.

19. An ozonized macadamia oil composition where ozone comprises between 50% and 95% of the total composition, whereby the composition is made by the method of claim 14.

20. The ozonized macadamia oil composition of claim 19, further comprising one of gadoleic or arachidic acid, C16 to C20 in a concentration between 0.05% and 8% of total weight.

21. The ozonized macadamia oil composition of claim 19, further comprising one of terpene aldehyde or monoterpene oxide in a concentration between 0.05% and 4% of total weight.

22. The ozonized macadamia oil composition of claim 19, further comprising one of 1,8 cineol, 16 methyl heptadecanoic acid, or 14 methyl hexadecanoic acid ma concentration between 0.05% and 3% of total weight.

23. The ozonized macadamia oil composition of claim 19 where said composition is a cream having a crystalline quality.

24. The ozonized macadamia oil composition of claim 19 where said composition can be applied topically to skin which has had its anatomical structure affected.

25. The ozonized macadamia oil composition of claim 19 where said composition is impregnated into a sterile cotton gauze to a point of saturation.

* * * * *